United States Patent [19]

Glimcher et al.

[11] Patent Number: 5,439,951

[45] Date of Patent: Aug. 8, 1995

[54] ISOLATION OF THE CALCIUM-PHOSPHATE CRYSTALS OF BONE

[75] Inventors: Melvin J. Glimcher, Boston; Hyun-Man Kim, Brookline, both of Mass.; Christian Rey, Castanet, France

[73] Assignee: Children's Medical Center Corporation, Boston, Mass.

[21] Appl. No.: 36,412

[22] Filed: Mar. 24, 1993

[51] Int. Cl.$^6$ .................. C08K 3/32; C08K 3/36; A61F 2/02; A61F 2/28

[52] U.S. Cl. .................. 523/115; 424/423; 424/426; 623/16; 264/344

[58] Field of Search .............. 424/423, 426; 623/16; 523/115; 264/344

[56] References Cited

U.S. PATENT DOCUMENTS 5,167,961  12/1992  Lussi et al. .................. 424/423

FOREIGN PATENT DOCUMENTS

| 2097409 | 4/1990 | Japan . |
| 03109210 | 5/1991 | Japan . |
| 4198007 | 7/1992 | Japan . |
| 92198007 | 7/1992 | Japan . |

OTHER PUBLICATIONS

Bonar, et al., "Structural and composition studies on the mineral of newly formed dental enamel; a chemical, x-ray diffraction, and $^{31}$P and proton nuclear magnetic resonance study", *J. Bone Min. Res.*, 6(11):1167–1176 (1991).

Cohen-Solal, et al., "Identification of organic phosphrous covalently bound to collagen and non-collagenous proteins of chicken-bone matrix: the presence of O--phosphoserine and O-phosphothreonine in non-collagenous proteins, and their absence from phosphorylated collagen", *Biochem, J.*, 177:81–98 (1979).

Costantino, P. D., et al., "Hydroxyapatite Cement-I. Basic Chemistry and Histologic Properties", *Arch. Otolaryngol. Head Neck Surg.*, 117(4):379–384 (1991).

Friedman et al., "Hydroxyapatite Cement-II> Obliteration and Reconstruction of the Cat Frontal Sinus", *Arch. Otolaryngol. Head Neck Surg.*, 117(4):385–388 (1991).

Glimcher, M. J., "A basic architectural principle in the organization of mineralized tissues" In: Milhaud, A.G., ed. Proceedings of the Fifth European Symposium on Calcified Tissues, Bordeaux, France, 1968.

Glimcher, M. J., "Molecular biology of mineralized tissues with particular reference to bone", *Rev. Mod. Physics*, 31:359–393. (1959).

Glowacki, J., et al., "The role of osteocalcin in osteoclast differentiation", *J. Cellular Biochem*, 45:292–302 (1991).

Glowacki, et al., "Demineralized Bone Implants", *Clin. Plast. Surg.*, 12(2):233–241 (1985).

Ripamonti, U., et al., "Xenogeneic osteogenin and demineralized bone matrices including human induced bone differentiation in athymic rats and baboons", *Matrix*, 11:404–411 (1991).

Ripamonti U., et al., "Induction of bone in composites of osteogenin and porous hydroxyapatite in baboons", *Plastic and Reconstructive Surg., 89:731-739 (1991).*

Sakae, et al., "Changes in bovine dentin mineral with sodium hypochlorite treatment", *J. Dental Res.*, 1229-1234 (1988).

(List continued on next page.)

Primary Examiner—Thurman K. Page
Assistant Examiner—Carlos Azpuru
Attorney, Agent, or Firm—Arnall Golden & Gregory

[57] ABSTRACT

The present invention is a process for first removing and isolating the calcium-phosphate crystals of bone from a substantial amount of the organic matrix and cellular constituents of bone without significant physical, chemical or structural alterations in the crystals. The crystals can then be further treated to remove the remaining amount of organic material associated with the crystals, leaving them essentially free of any of the organic constituents of bone, without significant physical, chemical or structural alterations in the crystals.

13 Claims, 1 Drawing Sheet

OTHER PUBLICATIONS

Landis, et al., "Electron microscopic observations of bone tissues prepared by ultracryomicrotomy", *J. Ultrastruct. Res.*, 59:185–206 (1977).

Landis, et al., "Electron diffraction and electron probe microanalysis of the mineral phase of bone tissue prepared by anhydrous techniques". *J. Ultrastruct. Res.*, 63:188–223 (1978).

Landis, et al., "Electron microscopic observations of bone tissue prepared anhydrously in organic solvents", J. Ultrastruct. Res., 59:1–30 (1977).

Lee and Glimcher, "Three-dimensional spatial relationship between the collagen fibrils and the inorganic calcium phosphate crystals of pickerel (*Americanus americanus*) and herring (*Clupea harengus*) bone", *J. Mol. Biol.*, 217:487–501 (1991).

Ohgushi, et al., "Repair of bone defects with marrow cells and porous ceramic", *Acta Orthop. Scand.*, 60(3):334–339 (1989).

Ono, et al., "Quantitative study on osteoconduction of apatite-wollastonite containing glass ceramic granules, hydroxyapatite granules, and alumina granules", *Biomaterials*, 11(4):265–271 (May 1990).

Passuti, et al., "Macroporous calcium phosphate ceramic performance in human spine fusion", *Clin. Orthop.*, 248:169–176 (1989).

Pinholt, et al., "Chemical, physical, and histologic studies on four commercial apatites used for alveolar ridge augmentation", *J. Oral Maxillofac. Surg.*, 50(8):859–867 (1992).; *J. Cariofac. Surg.*,* 1(3), 154–160 (Jul. 1990).

Pinholt, et al., "Alveolar ridge augmentation in rats by Bio-Oss", *Scand. J. Dent. Res.*, 99(2):154–161 (1991).

Ripamonti, U., et al., "Initiation of bone regeneration in adult baboons by osteogenin, a bone morphogenetic protein", *Matrix*, 12:369–380 (1992).

Sakae, T., et al., "Changes in Bovine Dentin Mineral with Sodium Hypochlorite Treatment", *J. Dental Research*, 67(9) 1228–1234 (Sep. 1988).

ISOLATION OF THE CALCIUM-PHOSPHATE CRYSTALS OF BONE

This invention was made with Government support under Grant #AR34081 awarded by the National Institutes of Health. The Government has certain rights in the invention.

BACKGROUND OF THE INVENTION

The present invention is generally in the area of purification of the naturally produced biological apatite crystals of bone, and of highly purified, calcium-phosphate apatite crystals of bone produced by these methods.

Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites. In general, the crystals of pure synthetic apatites, geological apatites and many impure synthetically produced apatites are larger and more crystalline than the biological crystals of bone, dentin, cementum and cartilage.

The calcium-phosphate (Ca—P) crystals of the bones of essentially all vertebrates have the basic crystal structure of hydroxyapatite $[Ca_{10}(PO_4)_6(OH)_2]$ as determined by x-ray diffraction. Indeed, the calcium-phosphate (Ca—P) crystals of essentially all of the normally mineralized tissues of vertebrates, including enamel, dentin, cementum, and calcified cartilage, have the same general crystal structure. There are few exceptions, notably the enamel of shark teeth which have fluoride ions substituted for many of the hydroxyl groups.

However, the crystals of Ca—P found in biological tissues such as bone also contain other atoms and ions such as acid phosphate groups ($HPO_4^{-2}$), and carbonate ions ($CO_3^{-2}$), which do not occur in pure, synthetic hydroxyapatite. There is also good evidence that bone crystals either do not contain hydroxyl groups, or contain only very few such groups (Bonar, et al., "Structural and composition studies on the mineral of newly formed dental enamel: a chemical, x-ray diffraction, and $^{31}P$ and proton nuclear magnetic resonance study" *J. Bone Min. Res.* 6:1167–1176 (1991), and is therefore more appropriately referred to as "apatite" rather than "hydroxyapatite". Moreover, many of the carbonate and phosphate groups in bone crystals are, from the structural and physical chemical points of view, unstable and very reactive, thus providing certain physical chemical and biological functional and chemical features important in the formation and dissolution of the crystals in biological tissues.

Recent important $^{31}P$-nuclear magnetic resonance spectroscopy studies have also demonstrated that the short-range order or environment of the $HPO_4^{-2}$ groups in bone crystals are distinctly different than the $HPO_4^{-2}$ groups in synthetic apatites and other related calcium-phosphate crystals (Wu, Ph.D. thesis M.I.T., "Solid state NMR study of bone mineral", August 1992). These differences in chemical, structural, and short range order of the bone crystals compared with pure, synthetic hydroxyapatite also reflect significant differences in their reactivity and hence in their potential function in a biological environment.

The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. This results in their having a very large surface area to present to the extracellular fluids which is critically important for the rapid exchange of ions with the extracellular fluids. This "ion-reservoir" function of the inorganic crystals is very important for a number of critical biological functions.

The vast majority of the Ca—P crystals of bone are located within the collagen fibrils of bone, as reported by Glimcher, M. J., "A basic architectural principle in the organization of mineralized tissues" In: Milhaud, A. G., ed. Proceedings of the Fifth European Symposium on Calcified Tissues, Bordeaux, France, 1968, Lee and Glimcher, "Three-dimensional spatial relationship between the collagen fibrils and the inorganic calcium phosphate crystals of pickerel (*Americanus americanus*) and herring (*Clupea harengus*) bone", *J. Mol. Biol.* 217:487–501 (1991); and Glimcher MJ, "Molecular biology of mineralized tissues with particular reference to bone" *Rev. Mod. Physics* 31:359–393 (1959). In general, bone contains approximately 35% organic constituents, the major component being collagen fibrils. See, for example, Cohen-Solal, et al., "Identification of organic phosphorus covalently bound to collagen and non-collagenous proteins of chicken-bone matrix: the presence of O-phosphoserine and O-phosphothreonine in non-collagenous proteins, and their absence from phosphorylated collagen" *Biochem, J,* 177:81–98 (1979). Due to their intimate physical location and interrelationship with the collagen fibrils, it has not heretofore been possible to separate and isolate the crystals of bone from the collagen fibrils of bone and other organic constituents of the tissue without producing significant changes in the chemistry, structure, degree of crystallinity and size of the crystals, as reported by Sakae, et al., "Changes in bovine dentin mineral with sodium hypochlorite treatment, *J. Dental Res.* 1229–1234 (1988).

Methods previously used to remove and isolate the calcium-phosphate apatite crystals of bone have not been successful, either because they do not completely separate the crystals from the organic constituents and/or because they alter the chemistry and structure of the crystals. For example, hydrazine treatment of well mineralized bone carried out at temperatures of 50° C. and higher yielded crystals containing significant amounts of organic constituents and induced significant changes in the crystals. Similarly, while substances such as sodium hypochlorite released calcium-phosphate apatite crystals from bone and other tissues, it was used in the form of an aqueous solution. Contact of bone crystals with water for even short periods of time has been shown to significantly alter the crystals by dissolution, reorganization, re-precipitation, and cannot be prevented by adding calcium and phosphate ions to the water based solution. See, for example, Landis, et al., "Electron microscopic observations of bone tissues prepared by ultracryomicrotomy" *J. Ultrastruct. Res.* 59:185–206 (1977); Landis, et al., "Electron microscopic observations of bone tissue prepared anhydrously in organic solvents" *J. Ultrastruct. Res.* 59:1–30 (1977); and Landis, et al., "Electron diffraction and electron probe microanalysis of the mineral phase of bone tissue prepared by anhydrous techniques" *J. Ultrastruct. Res.* 63:188–223 (1978) Furthermore, it has been found that the crystals are not only altered but also contains significant amounts of organic matrix. In a similar fashion, plasma ashing of bone to remove the organic matrix and disperse the crystals has been shown to induce major alterations in the crystal which as in the other methods described above can also contain significant amounts of organic constituents. Such treatment seriously alters the chemistry and structure of the crystals.

The synthetic materials are highly diverse, as reported in the literature. For example, the characterization of four commercial apatites was reported by Pinholt, et al., *J. Oral Maxillofac. Surg.* 50(8), 859–867 (August 1992); *J. Cariofac. Surg.* 1(3), 154–160 (July 1990) reports on a protein, biodegradable material; Pinholt, et al., *Scand. J. Dent. Res.* 99(2), 154–161 (April 1991) reports on the use of a bovine bone material called BiO-OSS TM; Friedman, et al., *Arch. Otolaryngol. Head Neck Surg.* 117(4), 386–389 (April 1991) and Costantino, et al., *Arch. Otolaryngol. Head Neck Surg.* 117(4), 379–384 (April 1991) report on a hydroxyapatite cement; Roesgen, *Unfallchirurgle* 16(5), 258–265 (October 1990), reports on the use of calcium phosphate ceramics in combination with atogeneic bone; Ono, et al., *Biomaterials* 11(4), 265–271 (May 1990) reports on the use of apatite-wollastonite containing glass ceramic granules, hydroxyapatite granules, and alumina granules; Passuti, et al., *Clin. Orthop.* 248, 169–176 (November 1989) reports on macroporous calcium phosphate ceramic performance; Harada, *Shikwa-Gakuho* 89(2), 263–297 (1989) reports on the use of a mixture of hydroxyapatite particles and tricalcium phosphate powder for bone implantation; Ohgushi, et al., *Acta Orthop. Scand.* 60(3), 334–339 (1989) reports on the use of porous calcium phosphate ceramics alone and in combination with bone marrow cells; Pochon, et al., *Z-Kinderchir.* 41(3), 171–173 (1986) reports on the use of beta-tricalcium phosphate for implantation; and Glowacki, et al., *Clin. Plast. Surg.* 12(2), 233–241 (1985), reports on the use of demineralized bone implants. No general conclusions can be drawn from these representative reports except that the need for materials which are useful in fixation of implants and in repair or replacement of bone defects remains and that the materials now available do not solve the many problems associated with the treatment of these problems, due to many variables, including the properties of the materials as well as the ease with which they can be manufactured and utilized by the surgeon.

The majority of synthetic hydroxyapatite preparations that have been proposed for use as bone inductors (to induce bone formation) and osteoconductors (by acting as scaffolds to facilitate for the continuous progression of new bone formation) are of synthetic origin and distinct structurally and chemically from the biological calcium-phosphate crystals in bone. All of these apatites are not only chemically and structurally distinct from the apatite crystals of bone, especially in their short range order, size and reactivity, but in some cases, they contain varying amounts of amorphous calcium-phosphate, that is, calcium-phosphate solids which are not crystalline at all. In other instances, the calcium-phosphates made synthetically also contain calcium salts other than apatite crystals such as calcium oxides. To date, it has not been shown how these additional calcium salts are biocompatible or without untoward effects, either biologically or structurally, nor how they affect the bonding strength between the synthetic apatites used to coat the surfaces of artificial joints implanted to bone and the surface of the artificial joint, and between the synthetic apatites and the bone into which the device is implanted.

It is therefore an object of the present invention to provide the biologically, naturally formed crystals of bone a purified apatite that are substantially free of organic material but which also consist predominantly of highly uniform crystals with respect to the chemistry, structure, size, shape and index of crystallinity.

It is a further object of the present invention to provide methods for the further purification of bone apatite crystals that remove essentially all organic material without disrupting the natural crystalline structure of the bone crystals.

SUMMARY OF THE INVENTION

The present invention is a process for removing and isolating the calcium-phosphate crystals of bone from a substantial amount of the organic matrix and cellular constituents of bone without significant physical, chemical or structural alterations in the crystals isolated from bone, cementum, dentin, enamel, and cartilage (referred to collectively herein as "bone"). The crystals can then be further treated to remove the remaining amount of organic material associated with the crystals, leaving them essentially free of any of the organic constituents of bone, without significant physical, chemical or structural alterations in the crystals, that is, having the same chemical composition, structure, short range order (as measured using standard techniques), and index of crystallinity as the native bone from which it is derived.

The calcium-phosphate (Ca—P) crystals (also referred to as "apatite") of bone are first isolated and purified by performing an initial separation to separate the crystals from the highly dense connective tissue in bone, then by reacting the dried bone powder with a polar solvent such as hydrazine at low temperatures. In young, poorly mineralized bone, the hydrazine step can be performed on the bone powder directly following grinding and milling at low temperatures. However, with more mature bone, the bone powder is first dispersed in a solvent such as ethanol, in the complete absence of water, and sonicated to achieve a gentle separation of organic matrix from bone crystals, then the crystals can be treated with hydrazine and/or plasma ashing at low temperatures. This process separates the crystals from the collagen fibrils and bundles of fibrils making up the densely packed tissue matrix, leaving the crystals relatively well dispersed and isolated from each other so that they are more readily accessible to chemical and/or physical techniques used to remove the remaining organic constituents without altering the crystal structure or chemistry. In either process, the bone particles can first be treated with plasma ashing.

Key aspects of the processes are that they do not utilize aqueous conditions at any point, they are performed at low temperatures, and they do not include any techniques inducing changes in the crystal structure or chemistry, such as high power sonication or grinding at warm temperatures.

These procedures yield isolated crystals free of collagen fibrils even from adult, heavily calcified, mature bone. The crystals have the signature characteristics of bone crystals in native bone, both analytically, chemically and structurally. Transmission electron microscopy reveals well dispersed crystals, free of any observable collagen fibrils or any other organic material. Chemical analysis, x-ray diffraction, and Fourier transform infrared spectroscopy show the typical characteristics of the crystals in native bone, including the presence of carbonate and acid phosphate groups, and the absence of hydroxyl groups as detected by Fourier transform infrared spectroscopy and proton nuclear magnetic resonance spectroscopy.

The isolated calcium-phosphate crystals are useful in a variety of applications, including chromatographic separation and isolation of proteins and in medical or therapeutic applications, such as in the healing and repair of bone, the replacement of bone with the eventual formation of new bone in the defects, and, in general, in the induction of new bone and in the osteoconductive progression of new bone formation, including the coating of specific surfaces of artificial joints or teeth implanted in bone.

DETAILED DESCRIPTION OF THE INVENTION

As used herein, "purified" and "purification" are not terms which are used to suggest that the apatite crystals are synthesized de novo in vitro; rather they refer to procedures to remove, disperse and isolate the natural, native, biological crystals which are in bone from bone, cementum, enamel, dentin and cartilage, without significantly altering their physical shape, size, structure or chemistry. They can be prepared so that their dry weight contains roughly as little as 25% or less of the total dry weight as organic matrix constituents or be further subjected to procedures which remove more of the organic constituents so that as little as approximately 2% or less of their dry weight is accounted for by organic constituents.

The exact determination of the size and habit of the extremely small calcium-phosphate (Ca—P) crystals in bone, and their short range order and fine structure, has been hampered because the crystals are embedded principally within collagen fibrils, which themselves are densely packed into fibers and fiber bundles of the highly organized extracellular matrix of the tissue fabric. Previous attempts to isolate the crystals free of the collagen fibrils and other organic matrix constituents by reaction with hydrazine and other reagents or by plasma ashing have left variable but significant quantities of organic matrix in the samples and have produced readily detectable and significant changes in the crystals.

Figure 1:
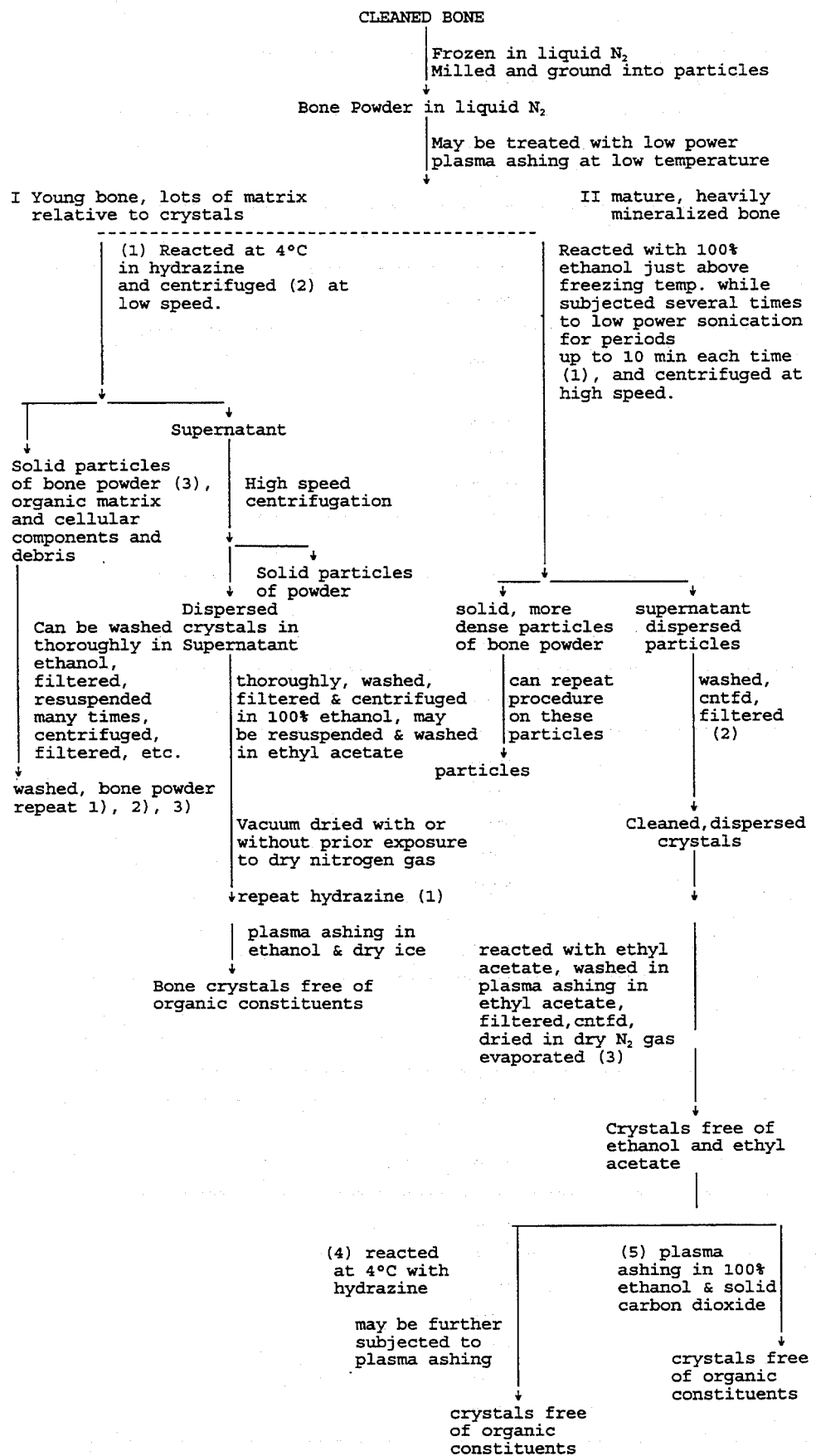
FIG. 1 is an abbreviated schematic flow chart of a general method for the separation and isolation of calcium-phosphate crystals from young, poorly mineralized bone (I) or more mature, more heavily mineralized bone (II).
Figure 1:
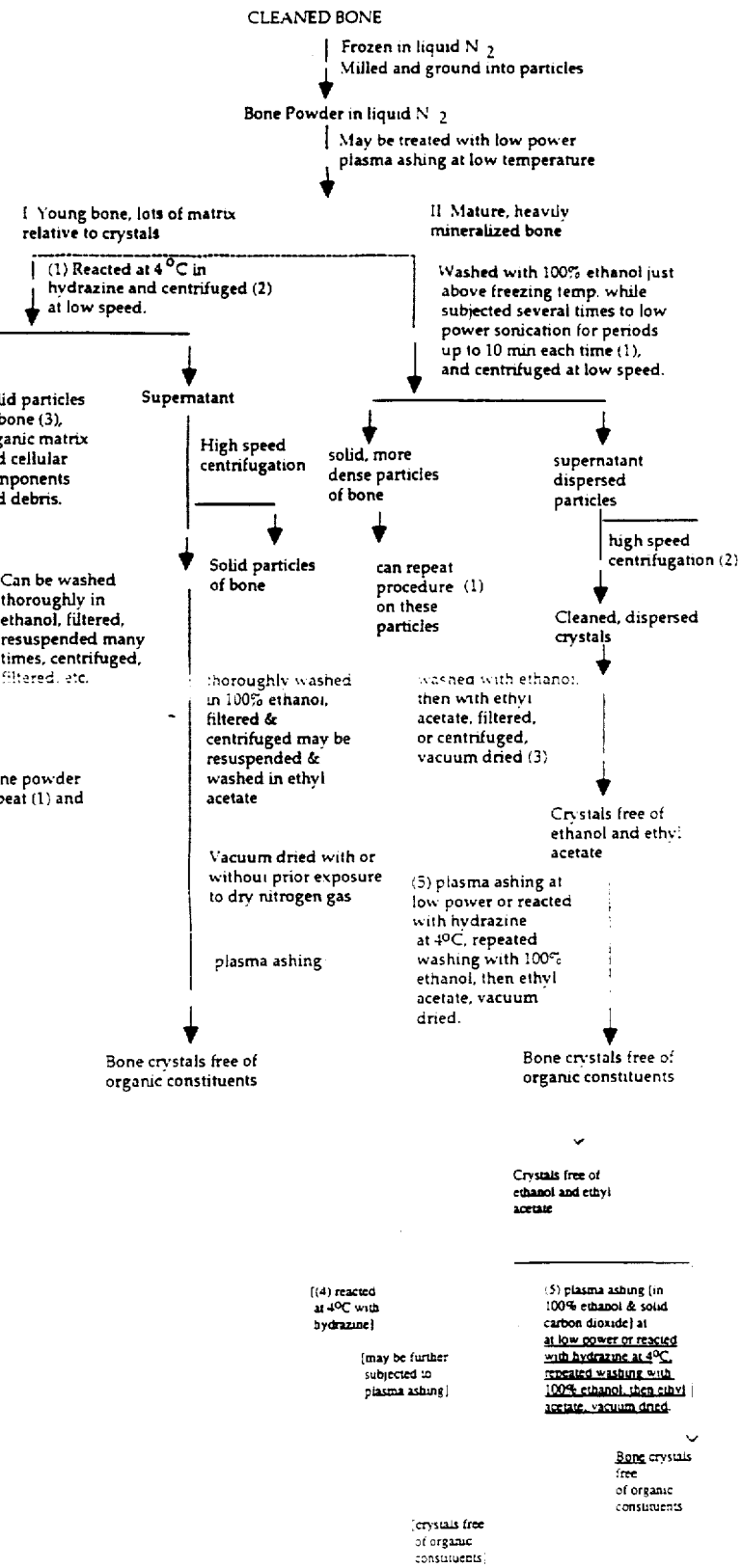

The methods described herein are shown schematically in FIG. 1, where (I) is the preferred process for use with young, not highly mineralized bone, and (II) is the preferred processes for use with more mature, and more mineralized bone. A combination of several of the above techniques can also be used depending on the level of mineralization of the tissue, the density of packing in the tissue, and other variables.

Isolation and Characterization of Calcium-phosphate Crystals from Bone

A method has been developed to remove and isolate the calcium-phosphate apatite crystals from bone that yields calcium-phosphate crystals that are essentially completely free of organic material and which have been shown not to have been significantly altered with regard to their structure or chemistry. As used herein, "bone" includes other biological sources of calcium-phosphate crystals including dentin, enamel, cementum and cartilage. "Purified" means separating and isolating the naturally occurring biological crystals in bone away from the organic matrix constituents, especially collagen fibrils, to less than 25%, most preferably less than 1%, of their total dry weight. The same procedures can be applied to other biologically calcified tissues such as the exoskeletons of invertebrates like coral which contain crystals of calcium carbonate. This material has also been used in combination with repair or replacement of bone.

Initial Isolation of Calcium-phosphate Crystals

The initial separation of the crystals of bone is accomplished by one of two different procedures, each of which may be preceded by a short period of treatment with low energy plasma ashing at low temperature. In the first, calcium-phosphate crystals of bone are isolated by reacting bone powder prepared by mill grinding fresh bone in liquid nitrogen and sieving to a particle size ranging up to approximately 200 microns, preferably 75 to 200 microns, with a polar non-aqueous solvent such as hydrazine ($NH_2$—$NH_2$) for varying periods of time at low temperatures, most preferably at 4° C. The crystals in the supernatant are separated from the solid bone particles by low speed centrifugation, resuspended in a polar organic solvent such as ethanol (methanol being too polar) and thoroughly washed, centrifuged and filtered in cold ethanol or other equivalent solvent.

The exact total times for mill-grinding the bone to a suitable particle size in liquid nitrogen which is critical to the process depends on the mass of bone used, the size of the gross pieces, and the density of the bone. In any case, milling must be done in short pulses, for example, of 5 to 15 seconds for small quantities of bone powder (50 mg), and for not too long a total time. One must monitor the specific processes for the specific type of bone, the amount of bone, and so forth, by transmission electron microscopy to make certain that processing has not caused changes in either the size, shape, or physical and chemical characteristics of the crystals. Importantly, none of the reagents or procedures used in processing of the crystals can include water. This is in contrast with other reported methods, for example, using sodium hypochlorite as a water based solution.

Transmission electron microscopy of the low speed ultracentrifuged supernatant from relatively young bone treated with hydrazine reveals dispersed crystals of similar size and shape to the Ca—P crystals observed in bone as well as collagen fibril-crystal aggregates, which can then be removed by high speed centrifugation, leaving only the dispersed crystals free of collagen fibrils as observed by electron microscopy. When these techniques are used with more calcified and mature bone, however, the yield of dispersed crystals is less than that obtained from the younger, less heavily mineralized bone.

A second procedure with a higher yield of isolated, dispersed crystals free of collagen fibrils and other organic constituents as observed by electron microscopy, can be obtained even from mature, normally calcified bone. This technique was developed based on observations that both aggregates of isolated crystals free of collagen fibrils and particles composed of aggregates of collagen and apatite crystals could be dispersed and separated from one another when they were gently sonicated for short periods of time in cold, organic polar solvent such as 100% ethanol using low energy sonication. In this procedure, the diaphyses of fresh long bones cleaned of periosteum and cartilage are frozen in liquid nitrogen, cut into gross pieces, and cleaned endosteally. The pieces of bone are ground in a mill in very short 5 to 30 second pulsed bursts in liquid nitrogen to a particle size of up to approximately 200 microns, preferably 75 to 200 microns. Total grinding time depends on the size of the initial gross pieces and the density of the bone (e.g., adult bovine bone compared with young chicken bone or small flexible fish bones). The dried bone powder is then suspended in solvent (ethanol) precooled to just above its freezing temperature, in a container jacketed to maintain the low temperature of the solvent and bone powder. Particles are subjected to several low power sonications, each period lasting up to 10 minutes, depending on the volume of ethanol and the total mass of bone powder utilized. This procedure can be repeated a number of times. The isolated crystals are then separated from the residual bone particles by high speed centrifugation, resuspended, then filtered and thoroughly washed with ethanol, centrifuged, then filtered and thoroughly washed with ethanol, centrifuged, filtered and dried by vacuum evaporation. The crystals are then suspended and washed in 100% ethyl acetate several times, then dried by passing dry $N_2$ gas over the crystals and finally by vacuum evaporation.

Characterization of Calcium-phosphate Crystals Obtained in Initial Separation

At this point in the preparation of the crystals, the crystals still have associated with them some residual organic constituents or breakdown products of the organic constituents, as shown by analytical chemical analyses, although electron microscopy reveals only the apatite crystals and no collagen fibrils or other organic components.

Both of the initial procedures, hydrazine reaction with young bone and sonication in organic polar solvent, yield isolated crystals free of collagen fibrils by electron microscopy. Chemical analysis, x-ray diffraction and Fourier transform infrared spectroscopy (FT-IR) of the crystals show no significant differences from analyses of whole, native bone, including the presence of carbonate and acid phosphate groups, and the failure to detect hydroxyl groups by fourier transform infrared spectroscopy and proton-nuclear magnetic resonance spectroscopy, signature characteristics of native, bone apatite crystals.

Further Processing to Remove Essentially All of the Organic Matrix Constituents from the Crystals Initially Isolated Two additional methods can be used to remove the remaining organic constituents. In the first method, the isolated crystals are suspended in hydrazine at a low temperature, preferably at 4° C., and reacted overnight. The crystals are then thoroughly washed in ethanol a number of times, and, as previously described, evaporated under vacuum, resuspended in ethyl acetate several times, and once again evaporated under vacuum and/or by passing dry $N_2$ over the crystals prior to vacuum evaporation. In the second method to remove the residual organic material remaining on the crystal surfaces, or as an additional procedure after treatment with hydrazine, the crystals are suspended in 100% ethanol or equivalent organic polar solvent, with solid carbon dioxide, and treated by low energy plasma ashing (for small quantities of bone, approximately 5 mg with low power defined as one watt or less, for 5 hours.

Applications for Purified Calcium-phosphate Crystals

Chromatographic Separations Applications

The isolated bone crystals can be used to purify and isolate biological molecules such as proteins, glycoproteins, carbohydrates, and nucleotides, by standard chromatographic and other analytical and preparative technologies. Synthetic apatites are already used for chromatography but performance varies from batch to batch and from producer to producer, depending on how the synthetic apatites are made, sized, and so forth.

The Ca—P crystals isolated as described herein are more uniform in size, chemical composition, and structure from the synthetic apatites, and differ from synthetic apatites because they have certain specific functional groups such as carbonate and acid phosphate moieties in specific locations and at specific energy levels as well as small amounts of other ions, many of which are on the surfaces of the crystals and in the case of bone crystals, for example, no detectable hydroxyl groups. Accordingly, they should provide more reproducible separations of specific components from a mixture of many components and also may be able to more selectively separate specific molecules originally present in the organic matrix of tissues such as bone and tooth with which they have specifically interacted in the native tissue as a result of these unique chemical and structural characteristics of the native bone crystals.

Therapeutic Applications

The purified calcium-phosphate crystals isolated from bone are useful as an aid to induce and promote bone healing. Synthetic apatite crystals have been shown to be biocompatible, both in vivo and in bone cell (osteoblast cell) cultures (Cordoba, et al., "Effect of microcrystalline hydroxyapatite on bone marrow stromal cell osteogenesis", Thirty Ninth Annual Meeting, Orthopaedic Research Society, 1993). There is also experimental evidence that synthetic apatite preparations can act as osteoinductors, biologically active materials which induce cells to form bone, and osteoinductors, biologically active materials which facilitate and provide a scaffolding on which bone formation can spread and advance.

Accordingly, the crystals have a variety of therapeutic applications, either alone or in conjunction with other substances bound to the crystals such as, for example, other bone cell inducers and stimulators, including the general class of cytokines such as the TGF-$\beta$ superfamily of bone growth factors (Cytokines and Bone Metabolism, Gowen, ed (CRC press, 1992), the teachings of which are incorporated by reference herein, (available from Boehringer-Mannheim), the family of bone morphogenetic proteins, osteoinductors, and/or bone marrow or bone forming precursor cells, isolated using standard techniques. With reference to sources and amounts of various materials that can be included with the crystals, see, for example, Glowacki, J., et al. "The role of osteocalcin in osteoclast differentiation" *J Cellular Biochem* 45:292–302 (1991); Ballock, T. T., et al. "Regulation of collagen expression in periosteal cells by three members of the TGF-B superfamily" *Thirty Ninth Annual Meeting, Orthopaedic Research Society;* 18,734 (1993); Ripamonti, U., et al. "Induction of bone in composites of osteogenin and porous hydroxyapatite in baboons" *J. Plastic and Reconstructive Surg.* 89:731–739 (1991); Ripamonti, U., et al. "Growth and morphogenetic factors in bone induction: role of osteogenin and related bone morphogenetic proteins" *CRC Critical Reviews in Oral Biol. Med.* 3:1–14 (1992); Ripamonti, U., et al. "Initiation of bone regeneration in baboons by osteogenin, a bone morphogenetic protein" *Matrix;* 12:40–55 (1992); Ripamonti, U., et al. "Xenogeneic osteogenin and demineralized bone matrices including human induced bone differentiation in athymic rats and baboons" *Matrix* 11:404–411 (1991); Cook, S. D., et al. "Restoration or large diaphyseal segmental defects in rabbits using recombinant human osteogenic protein (OP-1)" *Combined meetings of Orthopaedic Research societies of USA, Japan and Canada* 1, 66 (1991); Miyamoto, S., et al. "Trans-filter bone induction in monkeys by bone morphogenetic protein" *Thirty Ninth Annual Meeting, Orthopaedic Research Society* 18, 99 (1993); Yasko, A. W., et al. "Comparison of recombinant human BMP-2 versus cancellous bone to heal segmental bone defects" *Thirty Ninth Annual Meeting, Orthopaedic Research Society* 18, 100 (1993); Aspenberg, P., et al. "Bone morphogenetic protein induces bone in the squirrel monkey, but bone matrix does not" *Thirty Ninth Annual Meeting, Orthopaedic Research Society* 18, 101 (1993); Iwasaki, M., et al. "Bone morphogenetic protein-2 stimulates osteogenesis in high density culture of periosteum-derived cells" *Thirty Ninth Annual Meeting., Orthopaedic Research Society* 18, 483 (1993); Cook, S. D., et al. "Recombinant human osteogenic protein-1 (rhOP-1) heals segmental long-bone defects in non-human primates" *Thirty Ninth Annual Meeting, Orthopaedic Research Society* 18, 484 (1993); and Hunt, T. R., et al. "Healing of a segmental defect in the rat femur using a bone inducing agent (BIA) derived from a cultured human osteosarcoma cell line (SAOS-2)" *Thirty Ninth Annual Meeting, Orthopaedic Research Society* 18, 489 (1993), the teachings of which are incorporated by reference herein. The crystals can also be mixed with antibiotics or chemotherapeutic agents.

The isolated calcium-phosphate crystals are useful as an aid in the healing of bone defects, fractures, and other similar situations, or in the treatment of local bone resorption such as occurs in periodontal tissue or in the fixation of prosthetic implanted teeth into the bony jaws, especially when combined with substances which inhibit or lessen bone resorption such as isoleukin 1-$\beta$, for example, and osteoinductors such as the family of TGF-$\beta$. The crystals can be applied as a cement, in combination with a binder, preferably a biodegradable polymeric matrix, although non-biodegradable polyacrylate and cyanoacrylates are also useful, or as a paste. They can be sprayed or otherwise applied to the surface of prosthetics prior to or at the time of implantation, using in combination with an adhesive applied to the surface of the implant. They can also be used as filler in gaps in the bone resulting from trauma, infection, or cancer, using other materials to serve as structural supports until the crystals are replaced by newly formed bone. See, for example, Aberman, H. M., et al. "Gap healing in a non-weight bearing dog model: effectiveness of a solution precipitated apatite coating". *Thirty Ninth Annual Meeting, Orthopaedic Research Society* 18, 466 (1993).

A major complication of the use of artificial skeletal joints as implants and prosthetic teeth as implants in the loosening of artificial joint and tooth prostheses implanted into bone due to bony resorption about the implant. Examination of the surrounding tissues and prostheses has shown that this is due to the formation of cellular reactive connective tissue which forms after implantation and which incites resorption of the bone. This in turn is felt to be due for the most part to excessive micromotion between the implant and the living bone into which it is placed, presumably due to failure of sufficient interface appositional strength between the bone surface and the prosthesis. Recent work has also shown that when the appositional surfaces of the prosthesis are coated with apatite crystals, there is a significant increase in the appositional strength between the prosthetic surface and the implant and the surface of the bone which greatly diminishes the micromotion between the two components. See, for example, Bragdon, C. R., et al. "The histology of bone ingrowth at the implant/bone interface under known amounts of micromotion" *Thirty Ninth Annual Meeting, Orthopaedic Research Society* 18, 468 (1993); Burke, D. W., et al. "Mechanical aspects of the bone-porous surface interface under known amounts of implant motion: an in vivo canine study" *Thirty Ninth Annual Meeting, Orthopaedic Research Society* 18, 470 (1993); and Hollis, M. J., et al. "Effect of micromotion on ingrowth into porous coated implants" *Thirty Ninth Annual Meeting, Orthopaedic Research Society* 18, 472 (1993).

The crystals can be used in powdered form, shaped into blocks of ceramic, porous coatings, or mixed with other materials for use as coatings or cements, using the methods and materials known to those skilled in this art. These are then useful for the manufacture of artificial prostheses, coatings on artificial joints or implanted prosthetic teeth and using the biological bone crystals embedded and combined with a biodegradable carrier. Components which induce bone formation and others which diminish bone resorption as well as antibiotics and other chemotherapeutic agents can be combined with the apatite crystals.

To date, there is no available detailed analysis of the intricate chemistry and structure of the synthetic apatites used to coat the prostheses. Although the methods of preparation of the synthetic apatites varies, they are generally formulated and applied to the metallic surfaces of the implants by plasma spraying which results not only in the formation of crystalline hydroxyapatites (but of varying chemical composition) and what has been term "amorphous" calcium-phosphates as well as calcium salts in addition to calcium-phosphate apatites. The specific chemical and physical characteristics of the native or natural calcium-phosphate crystals of bone isolated from bone formulated to allow for increased bone formation (i.e. bone induction) and osteoinduction should not only permit a much increased interfacial appositional strength and bond between the bony surfaces and the implanted device (joint or tooth implant) but also allow a more bony bonding between the implant and the bone into which the implant is placed.

In all of these applications, care should be taken not to alter or damage the crystals, for example, by exposure to high temperatures and water.

Modifications and variations of the present invention will be obvious to those skilled in the art from the foregoing detailed description. Such modifications and variations are intended to come within the scope of the appended claims.

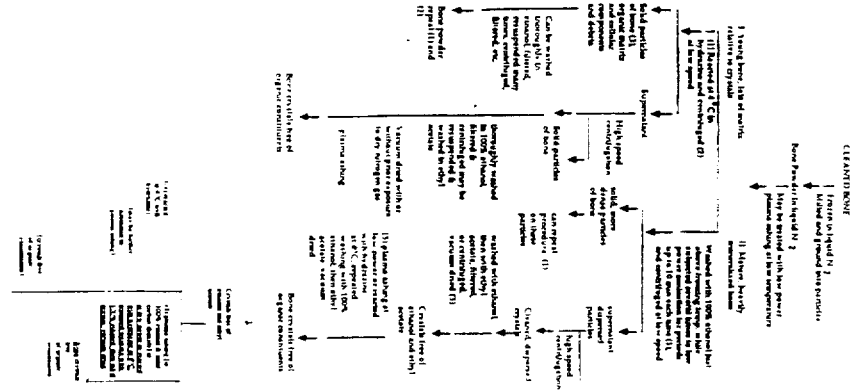

We claim:

1. A method for isolating calcium-phosphate apatite crystals from bone which avoids exposure of the crystals to water comprising the steps of
   grinding in the absence of water at a temperature equivalent to liquid nitrogen clean bone pieces into particles ranging in size of up to approximately 200 microns, where the bone is selected from the group consisting of bone, cartilage, cementum, dentin, and enamel;
   separating the calcium-phosphate crystals in the bone from the collagen fibrils in the bone by sonication of the particles suspended in a non-aqueous solvent which is less polar than methanol for the collagen fibrile but not the crystals at a temperature just above the freezing temperature of the solvent; and
   separating the non-aqueous solvent and collagen fibrils from the calcium phosphate crystals.

2. The method of claim 1 further comprising
   removing the remaining organic material from the calcium phosphate crystals in the absence of water to form crystals containing less than 2% of the total dry weight as organic material.

3. The method of claim 2 wherein the remaining organic material is removed by reaction with an polar non-aqueous solvent under conditions equivalent to reaction with hydrazine at 4° C.

4. The method of claim 2 wherein the remaining organic material is removed by plasma ashing.

5. The method of claim 1 wherein the bone is mature, mineralized bone further comprising plasma ashing and reacting the purified bone particles with an organic solvent equivalent to hydrazine wherein the method comprises the steps of
   grinding in the absence of water at a temperature equivalent to liquid nitrogen clean bone pieces into particles ranging in size of up to approximately 200 microns, where the bone is selected from the group consisting of bone, cartilage, cementum, dentin, and enamel;
   plasma ashing of the ground bone particles;
   separating the calcium-phosphate crystals in the bone from the collagen fibrils in the bone by sonication of the particles suspended in a non-aqueous solvent for the collagen fibrils, wherein the solvent is less polar than methanol, but not the crystals at a temperature just above the freezing temperature of the solvent;
   separating the non-aqueous solvent and collagen fibrils from the calcium phosphate crystals; and
   reacting the purified bone particles with an organic solvent equivalent to hydrazine.

6. The method of claim 1 wherein the crystals are derived from immature bone.

7. The method of claim 1 wherein the non-aqueous solvent is anhydrous 100% ethanol and the calcium-phosphate crystals are separated from the collagen fibrils by centrifugation.

8. The method of claim 1 wherein the crystals which are separated from the collagen fibrils are irregularly shaped, very thin plates whose rough average dimensions are approximately 10 to 50 angstroms in thickness, 30 to 150 angstroms in width, and 200 to 600 angstroms in length.

9. A method of making a calcium-phosphate crystalline implant comprising the steps of
   grinding at a temperature equivalent to liquid nitrogen clean bone pieces into particles ranging in size of up to approximately 200 microns, where the bone is selected from the group consisting of bone, cartilage, cementum, dentin, and enamel;
   separating the calcium-phosphate crystals in the bone from the collagen fibrils in the bone by sonication of the particles suspended in a polar non-aqueous solvent for the collagen fibrils but not the crystals at a temperature just above the freezing temperature of the solvent;
   separating the non-aqueous solvent and collagen fibrils from the calcium phosphate crystals; and
   adding to the crystals an adhesive or binder to form a calcium-phosphate crystalline cement or paste.

10. The method of claim 9 further comprising applying the crystals to the surfaces of solid materials for implantation.

11. The method of claim 9 further comprising forming the crystals into ceramic blocks for implantation into gaps or areas of bone resorption.

12. The method of claim 9 further comprising adding to the crystals a biologically active molecule selected from the group consisting of bone morphogenic proteins, cytokines, antibiotics, chemotherapeutic agents, and bone marrow or bone progenitor cells.

13. The method of claim 11 wherein the process is applied to coral to remove the organic material from the calcium carbonate forming the coral structure.

* * * * *

UNITED STATES PATENT AND TRADEMARK OFFICE
CERTIFICATE OF CORRECTION

PATENT NO. : 5,439,951

DATED : August 8, 1995

INVENTOR(S) : Melvin J. Glimcher, et al.

It is certified that error appears in the above-identified patent and that said Letters Patent is hereby corrected as shown below:

The title page, should be deleted to appear as per attached title page.

The sheet of drawing, consisting of figure 1, should be deleted to appear as per attached sheet.

Signed and Sealed this

Twenty-third Day of January, 1996

Attest:

BRUCE LEHMAN

*Attesting Officer*     *Commissioner of Patents and Trademarks*

ISOLATION OF THE CALCIUM-PHOSPHATE CRYSTALS OF BONE

[75] Inventors: Melvin J. Glimcher, Boston; Hyun-Man Kim, Brookline, both of Mass.; Christian Rey, Castanet, France

[73] Assignee: Children's Medical Center Corporation, Boston, Mass.

[21] Appl. No.: 36,412

[22] Filed: Mar. 24, 1993

[51] Int. Cl.⁶ .................... C08K 3/32; C08K 3/36; A61F 2/02; A61F 2/28
[52] U.S. Cl. ........................ 523/115; 424/423; 424/426; 623/16; 264/344
[58] Field of Search .............. 424/423, 426; 623/16; 523/115; 264/344

[56] References Cited

U.S. PATENT DOCUMENTS 5,167,961 12/1992 Lussi et al. ............................ 424/423

FOREIGN PATENT DOCUMENTS

| 2097409 | 4/1990 | Japan |
| 03109210 | 5/1991 | Japan |
| 4198007 | 7/1992 | Japan |
| 4219800 | 7/1992 | Japan |

OTHER PUBLICATIONS

Bonar, et al., "Structural and composition studies on the mineral of newly formed dental enamel; a chemical, x-ray diffraction, and $^{31}P$ and proton nuclear magnetic resonance study", *J. Bone Min. Res.*, 6(11):1167–1176 (1991).

Cohen-Solal, et al., "Identification of organic phosphrous covalently bound to collagen and non-collagenous proteins of chicken-bone matrix: the presence of O-phosphoserine and O-phosphothreonine in non-collagenous proteins, and their absence from phosphorylated collagen", *Biochem. J.*, 177:81–98 (1979).

Costantino, P. D., et al., "Hydroxyapatite Cement-I. Basic Chemistry and Histologic Properties", *Arch. Otolaryngol. Head Neck Surg.*, 117(4):379–384 (1991).

Friedman et al., "Hydroxyapatite Cement-II> Obliteration and Reconstruction of the Cat Frontal Sinus" *Arch. Otolaryngol. Head Neck Surg.*, 117(4):385–388 (1991).

Glimcher, M. J., "A basic architectural principle in the organization of mineralized tissues" In: Milhaud, A.G. ed. Proceedings of the Fifth European Symposium on Calcified Tissues, Bordeaux, France. 1968.

Glimcher, M. J., "Molecular biology of mineralized tissues with particular reference to bone", *Rev. Mod Physics*, 31:359–393, (1959).

Glowacki, J., et al., "The role of osteocalcin in osteo clast differentiation", *J. Cellular Biochem.* 45:292–301 (1991).

Glowacki, et al., "Demineralized Bone Implants", *Clin Plast. Surg.*, 12(2):233–241 (1985).

Ripamonti, U., et al., "Xenogeneic osteogenin and de mineralized bone matrices including human induced bone differentiation in athymic rats and baboons", *Matrix*, 11:404–411 (1991).

Ripamonti U., et al., "Induction of bone in composite of osteogenin and porous hydroxyapatite in baboons" *Plastic and Reconstructive Surg.*, 89:731–739 (1991).

Sakae, et al., "Changes in bovine dentin mineral with sodium hypochlorite treatment", *J. Dental Res.* 1229–1234 (1988).

(List continued on next page.)

Primary Examiner—Thurman K. Page
Assistant Examiner—Carlos Azpuru
Attorney, Agent, or Firm—Arnall Golden & Gregory

[57] ABSTRACT

The present invention is a process for first removing and isolating the calcium-phosphate crystals of bone from a substantial amount of the organic matrix and cellular constituents of bone without significant physical, chemical or structural alterations in the crystals. The crystals can then be further treated to remove the remaining amount of organic material associated with the crystals, leaving them essentially free of any of the organic constituents of bone, without significant physical, chemical or structural alterations in the crystals.

13 Claims, 1 Drawing Sheet